Figure 1:
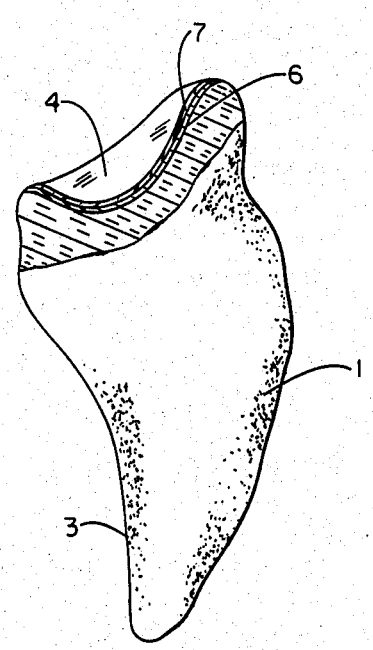

United States Patent [19]

Breustedt et al.

[11] Patent Number: 4,523,912
[45] Date of Patent: Jun. 18, 1985

[54] MINERAL TOOTH WITH SILANE-COUPLED ADHESIVE PLASTIC PART

[75] Inventors: Alfred Breustedt, Berlin; Heinz Täschner, Radeberg; Rainer Korf, Radeberg; Renate Lorenz, Radeberg, all of German Democratic Rep.

[73] Assignee: VEB Kombinat Medizin-und Labortechnik Leipzig, Leipzig, German Democratic Rep.

[21] Appl. No.: 474,089

[22] Filed: Mar. 10, 1983

Related U.S. Application Data

[63] Continuation of Ser. No. 415,770, Sep. 7, 1982, abandoned, which is a continuation-in-part of Ser. No. 164,757, Jun. 30, 1980, abandoned.

[30] Foreign Application Priority Data

Jun. 29, 1979 [DD] German Democratic Rep. ... 213978

[51] Int. Cl.$^3$ .............................................. A61K 6/08
[52] U.S. Cl. .................................... 433/202; 433/199; 433/201; 433/212; 260/998.11; 523/115
[58] Field of Search ............... 433/202, 212, 201, 199; 264/19, 20; 260/998.11; 523/115

[56] References Cited

U.S. PATENT DOCUMENTS

| | | | |
|---|---|---|---|
| 2,705,836 | 1/1949 | Watson | 433/212 |
| 3,423,829 | 1/1969 | Halpern et al. | 433/212 |
| 3,423,831 | 1/1969 | Semmelmon | 433/212 |
| 3,453,349 | 4/1984 | Cannan | 260/998.11 |
| 3,709,866 | 1/1973 | Waller | 523/115 |
| 4,089,763 | 5/1978 | Dart et al. | 523/212 |
| 4,182,035 | 1/1980 | Yamauchi et al. | 433/228 |
| 4,281,991 | 8/1981 | Michl et al. | 523/115 |
| 4,383,826 | 5/1983 | Butler et al. | 433/202 |
| 4,451,235 | 5/1984 | Okuda et al. | 260/998.11 |

Primary Examiner—John Kight
Assistant Examiner—Garnette D. Draper
Attorney, Agent, or Firm—Jordan and Hamburg

[57] ABSTRACT

The invention concerns a mineral tooth having a silane-coupled adhesive plastic part which enables chemical bonding with base materials being common in dental prosthetics as well as a process for its industrial manufacture.

The ground masses of the individual layers of the mineral tooth have grain sizes with a fractionation from about 60 µm to about 100 µm and the adhesive plastic part consists of a multiple component mixture of suitable viscosity and consistency and with 1% to 5% of mineral filler material.

With fritting of the ground masses, a defined guidance of both time and temperature is carried out in the range from 600° C. to 900° C., the mineral teeth are silanized for several times in the silane solution and the multiple component mixture is applied without pressure on the mineral tooth and is polymerized-on without pressure by means of a source of heat rays.

19 Claims, 6 Drawing Figures

MINERAL TOOTH WITH SILANE-COUPLED ADHESIVE PLASTIC PART

This application is a continuation of application Ser. No. 415,770, filed Sept. 7, 1982, now abandoned, which, in turn, is a continuation-in-part of application Ser. No. 164,757, filed June 30, 1980, now abandoned.

PROCESS OF ITS MANUFACTURE

The invention concerns a mineral tooth with silane-coupled adhesive plastic part, which allows chemical bonding to base materials being common in dental prosthetics. Furthermore the invention concerns a process for its industrial manufacture.

CHARACTERISTIC FEATURES OF KNOWN TECHNICAL SOLUTIONS

Mineral teeth having either pin-anchoring or diatonic or dovetail anchoring and their manufacturing processes are known. Their disadvantage consists in the weakening of the mineral teeth-bodies due to the feasible possibilities of anchoring, in the limitation of the complete anatomical formation of these and consists in particular in the mechanical linking material being the only possible method between mineral tooth and base. These disadvantages are contrasted by particularly favorable characteristics of the chosen minerals and by the command of matured technological processes in the manufacture of mineral tooth.

Also known is the manufacture of plastic teeth made of Methylmethacrylates by either thermo- or chemoplastic procedures which enable chemical bonding between the base materials of dental prosthetics. The disadvantages of such artificial teeth consist in too rapid abrasion, susceptibility to action of chemical substances and in easy water uptake. These result in undesirable phenomena of aging, which besides abrasion, becomes apparent by discoloring and deposits of films (settlement of bacteria). By admixture of cross-linking agents (e.g. Glycoldimethylacrylate or of butandiole-1,4-dimethylacrylate) it is possible to counteract these negative properties of plastic teeth. If a certain degree of interlacing is surpassed however, a chemical resistance is achieved to such an extent which still enables mechanical joining to the base material only, resulting thereby in an essential disadvantage being common with mineral teeth.

With the development of silanes by the application of which as an adhesive the affinity of mineral bodies and of plastic materials was achieved, new aspects arose in favor of dental prosthetics also.

According to document DE-OS No. 15 66 206, which corresponds to Semmelman U.S. Pat. No. 3,423,831, an artificial tooth is known which consists of dental-ceramic and of a synthetic resin part, whereby at least one part of the edge lobules extending to the tooth and the wall surfaces consists of synthetic resin and this part is completely joined to the ceramic part of the tooth by silane material. The distribution of the strain of the composed tooth is a favorable one if the resin part is put on as an overlay instead of an inlay. The resin part extends at least over the half length of the lingual surface of the unprotected tooth or to incisally from the edge lobule surface of the tooth.

According to document DE-OS No. 19 03 935, which corresponds to Halpern et al U.S. Pat. No. 3,423,829, an artificial tooth is known, which consists of an external shell made of aesthetic porcelain and of an internal core made of a synthetic resin. The core of resin and the porcelain-shell are chemically joined at their boundary layer by a polymerizable organo-silicon compound.

Furthermore according to document DE-OS No. 19 44 930 an artificial tooth made of porcelain is known, which is provided with a deep excavation or recess. The excavation is situated in the centre of the connective surface of the tooth and separates this into two zones. A first zone consists of a peripheral rim-surface of the tooth and the second zone is a connective surface reaching centrally far to inwards to form the excavation. To the connective surface in the laboratory an adhesive silane layer is applied resulting in a firm linkage between porcelain tooth and plastic bridge. The excavation is bigger than this part which the laboratory technician has to remove in the most unfavorable case. The excavation may be filled in addition with an inlay of plastic, which secures firm adherence to the plastic bridge. However as with a mechanically anchored mineral tooth, indentations, grooves, undercuts will weaken the tooth body and increase the risk of breakage. Teeth being designed in this manner do not offer any advantage with the preparation of molds for the industrial manufacture of mineral teeth and are limiting to a large extent the approximation to the completely anatomically shaped natural prototype. For applying of the plastic parts on silane-treated mineral teeth the procedures are described which are common with the processing of cold- and hot polymerisates. This has the disadvantage that these procedures are unsuitable to rational manufacture and thus for industrial use and because of the fact that the absolute safety of the linkage between silane-treated mineral teeth and plastic material may not be reproduced in large scale production in a reliable manner. An essential reason for this are the different stress strain relations of mineral bodies and of methacrylates. The immense expenditure of the outfits and pressing molds, the complicated possibilities of technological solutions and the uncertainty of reproducibility of a stable linkage between silane-treated mineral teeth and plastic material are decisive reasons for the fact that the utilization is not put on an industrial large scale but is limited to dental laboratory institutions only.

AIM OF THE INVENTION

The aim of the invention consists in elimination of the disadvantages of the known solutions and in the development of an artificial mineral tooth having a plastic adhesive part, which may be processed in the dental laboratory without additional expenditure like a plastic tooth, as well as in the development of a process which enables the industrial manufacture of the mineral tooth with a plastic adhesive part.

DEMONSTRATION OF THE ESSENTIAL FEATURES OF THE INVENTION

The task of the invention consists in the formation of the artificial tooth in an almost completely anatomical manner and with a high degree of firmness, in the application of an adhesive plastic part being selected with respect to its composition to the mineral tooth by means of a chemical compound as well as to provide for a process for the industrial manufacture of the linkage between plastic adhesive part and mineral tooth.

According to the invention the problem is solved by the fact that the ground masses of the individual layers of the mineral tooth have grain sizes with a fractionation from <60 μm to ≦100 μm, that after having applied a silane layer on the dorsal and basal surfaces of the mineral tooth, the plastic adhesive part has to be put on and that the adhesive plastic part consists of a multiple component mixture made of 30 to 33% polymethacrylic acid methylester, 3% to 6% dioxane, 63% to 66% methacrylic acid methylester, 1% to 2% of a sensitizer and 0.3–1% of a vapor pressure reducing substance. The multiple component mixture may contain 1% to 5% mineral filler material or previously silanized mineral fillers of a grain size of <60 μm or silicate bonded color pigments.

A suitable sensitizer is disclosed in DDR-WP No. 84,929 to Gürtler et al, entitled "Method for the Manufacture of Polymerization Products Based on Special Unsaturated Polyester Resins through UV-Radiation" issued Oct. 5, 1971. In particular, the sensitizer in that patent is a compound of the formula

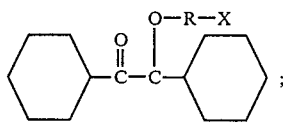

wherein R may represent an alkylene group, an alkylene ether group, or poly-alkylene ether groups, and X may represent hydrogen, a hydroxy group, or a halogen. A suitable vapor pressure reducing substance is a pineapple-aroma concentrate of a production No. 512,027 in the German Democratic Republic and is made up of the following ingredients:
allyl capronate
allyl mustard oil
phenylethylvalerianate
ethyl benzoate
benzyl butyrate
Benzyl valerianate
Terpinyl acetate
amyl butyrate
ethyl propionate
ethyl butyrate
citral
geraniol
ethyl acetate
vanillin
triacetin
ethanol The problem of the process according to the invention is solved by the fact that with fritting of the ground masses for the individual layers of the mineral tooth in the range between 600° C. and 900° C. a determined guidance of time and temperature is carried out, that the mineral tooth by multiple insertion and movements in the silane solution and by immediately ensuing drying between the preparation and at the end of the process of silanization becomes silanized and that the multiple component mixture is preferably applied to the dorsal and basal surfaces respectively of the previously silanized mineral tooth without any pressure and is polymerized-on using a source of heat rays at temperatures of T from 20° to 50° C. and with durations of time from 3 to 6 minutes. It is advantageous the dorsal and basal sections respectively of the mineral tooth which accommodates the adhesive plastic part has a boundary to laterally of a circular shape.

Preferably the silane solution consists of γ-aminopropyltriethoxysilane, γ-glycidyloxipropyltrimethoxysilane or of γ-methacryloxypropyltrimethoxysilane in an acetic acid containing medium. The silane solution is a 1% water solution in a 0.3% acetic acid solution. γ-methacryloxypropyltrimethoxysilane is the preferred silane. The silane solution may be produced by mixing the silanes and the 0.3% acetic acid in a ratio of about 1:99.

FORM OF CONSTRUCTION CITED BY WAY OF PATENT SPECIFICATION

Figure 2:
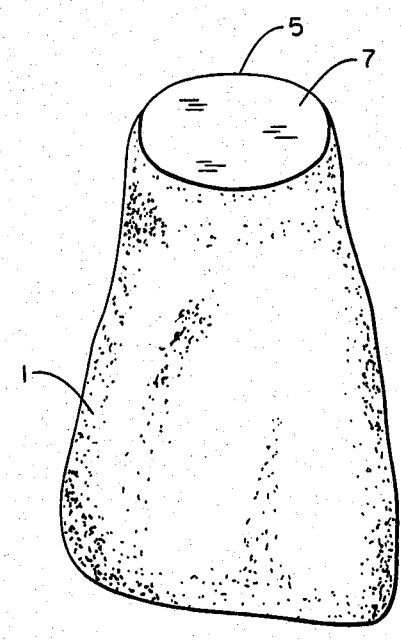

In the following the invention should be illustrated more closely using an exemplified embodiment. In the pertaining drawing is shown by FIG. 1 a lateral view of a mineral incisor tooth FIG. 2 a rear view of the mineral incisor tooth from FIG. 1

Figure 3:
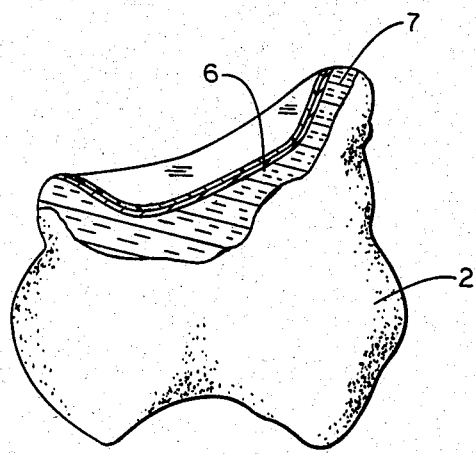

FIG. 3 a lateral view of a mineral molar tooth

Figure 4:
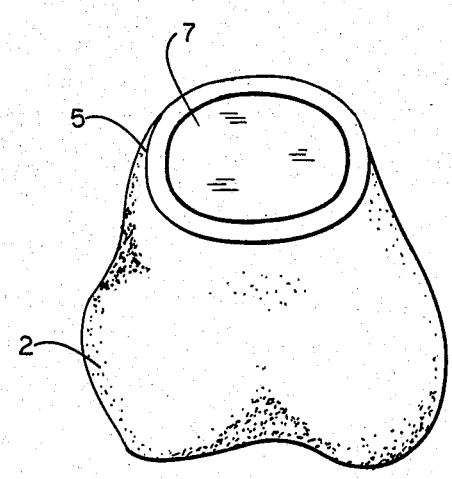

FIG. 4 a rear view of the mineral molar tooth from FIG. 3

Figure 5:
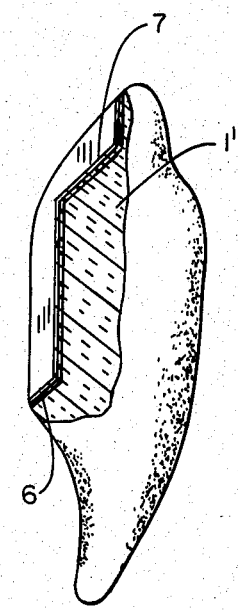

FIG. 5 a mineral incisor tooth as manufactured in a conventional mold

Figure 6:
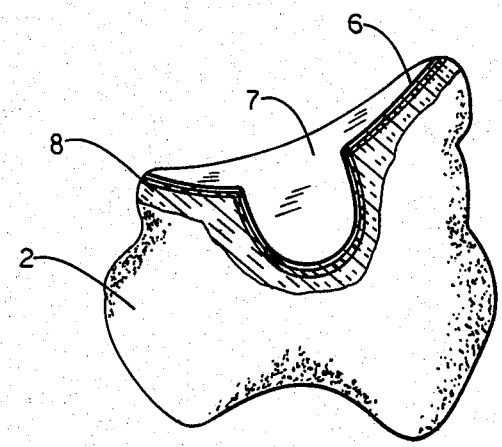

FIG. 6 a mineral molar tooth as manufactured in a conventional mold

The mineral incisor tooth 1 as represented in FIG. 1 as well as the mineral molar tooth 2 as represented in FIG. 3 are almost completely shaped according to anatomy. The dorsal surface 3 and the basal surface 4 show a lateral circular boundary 5. To this dorsal surface 3 and to this basal surface 4 a silane solution is applied, which consists of γ-aminopropyltrimethoxysilane or γ-methacryloxypropyltrimethoxysilane in an acetic acid containing medium. The silane layer 6 causes a firm chemical bonding between the mineral tooth 1, 2 and an adhesive plastic part 7. The adhesive plastic part consists of a multiple component mixture made up of 30% to 33% polymethacrylic acid methylester, 3% to 6% dioxane, 63% to 66% methacrylic acid methylester, 1% to 2% of a sensitizer and 0.3–1% of a vapor pressure reducing substance.

The multiple component mixture may contain 1% to 5% of mineral filler material or 1% to 5% previously silanized mineral fillers such as quartz or aluminium oxide ($Al_2O_3$) with grain sizes of <60 μm.

The preferred composition of the multiple component mixture is as follows:
polymethacrylic acid methyl ester: 30.5%
methacrylic acid methyl ester: 63.9%
dioxane: 4.0%
UV sensitizer: 1.3%
vapor pressure reducing substance: 0.3%

The adhesive plastic part 7 enables simple chemical bonding of the mineral tooth 1, 2 to a base material being usual in dental prosthetics and is shaped in a manner which enables that in spite of maximal grinding of the dorsal surface 3 and the basal surface 4 respectively for the purpose of adaptation to a plastic prosthesis (not represented in the drawing), a firm linkage between mineral tooth 1, 2 and prosthesis is still guaranteed.

Both stress strain relations among the mineral layers of a tooth and also the stress strain relation between the dorsal layer 3 and basal layer 4 of the mineral tooth 1, 2 and of the adhesive plastic part 7 applied to it, are of great importance for the achievement of high and constant tension and bending strength values.

By a suitable choice of different grain sizes with a fractionation from <60 μm to ≦100 μm for the set up of layers of the mineral teeth, defined guidance with respect to time and temperature in the range between 600° C. and 900° C. with fritting of the masses for the individual layers of the mineral tooth after the final burning internal tensions are generated within the tooth resulting in a high firmness.

It is necessary to select such a structure for the dorsal and basal layers respectively of the tooth, accommodating the adhesive plastic part which due to its special chemical composition is adapted to the behavior of expansion of the adhesive plastic part and results in an as large as possible surface. The up to three times as large surface as compared to conventional mineral teeth is achieved by means of a defined mixture of previously fritted masses with different fractionation.

Prior to silanizing the mineral teeth 1, 2 have to be washed using xylol and ultra sonics in order to guarantee an absolutely fat-free and clean surface. Subsequent to this, the mineral teeth 1, 2 are inserted at least twice in the silane solution and are moved within it. After any silanization, the mineral teeth 1, 2 are dried. After-treatment may achieve that undesired affinity outside of the adhesive plastic zone becomes abolished. The multiple component mixture for the adhesive plastic part 7 being controlled in its viscosity-behavior and to be applied to the silanized dorsal section 3 and basal section 4 respectively, possesses a consistency which guarantees that the mixture does not run away and may be directed and applied to areas and zones respectively. The lateral circular boundary 5 of the dorsal surface 3 and basal surface 4 respectively enables the well-defined application of the adhesive plastic part 7 on the mineral tooth 1, 2. Using a source of heat rays, the multiple component mixture is polymerized-on with temperature between 20° C. and 50° C. during a period of 3 to 6 minutes. If to the multiple component mixture for the plastic part e.g. previously silanized mineral filler materials or silicate bonded color pigments having grain sizes of <60 μm are added, the behavior of tension between mineral tooth and adhesive plastic part at the one hand and between adhesive plastic part at the other hand, may be influenced. Under these conditions these silanized added particles act like retaining pearls with respect to the base material. By the admixture of silicate bonded color pigments the possibility exists to adapt the adhesive plastic part to the color of the mineral tooth. It is however, also possible to use the already existent molds without extensive alterations. FIG. 5 shows a mineral front tooth 1' which was manufactured in a conventional mold, which analogous to the almost completely anatomical mineral incisor tooth 1 is provided with a silane layer 6 and is linked with an adhesive plastic part 7. The mineral molar tooth 2' as illustrated in FIG. 6 is likewise pressed in a conventional mold without diatonic undercut. Thereby the adhesive plastic part 7 completely fills up the excavation 8.

The following is a more detailed description of the procedure for preparing the mineral tooth with silane-coupled adhesive plastic part:

1. The mineral teeth are degreased by means of a degreasing component, e.g. 1,1,2-Trifluoro-trichlorethane. The degreasing takes place in an ultrasonic bath for 10 minutes. Thereafter, the degreased mineral teeth are dried in an air stream for approximately 5 minutes.

2. The mineral teeth are silanized in a silane solution. They are added to the solution and joggled. Time: approximately 5 minutes. Thereafter they are dried in a drying cabinet at temperatures of 110° C. and for 10 minutes. This process is repeated a second time.

3. When the silanized teeth are cooled off, the adhesive plastic part is introduced. This is done by manually applying the multiple component mixture from a measuring bottle to the outlined dorsal and basal surfaces of the mineral tooth. The consistency of the multiple component mixture guarantees that the mixture does not flow away and that it can be applied spotwise. The process time of up to 120 hours is a good prerequisite for its industrial usefulness.

Polymerizing of the adhesive plastic part and the multiple component mixture is done by using UV-rays. The radiation takes place under a quartz lamp at temperatures of 20° C. to 50° C. for a time period of 4 minutes and under normal atmospheric conditions (pressure-free). It is thus not polymerized via vacuum or under pressure. The polymerization time of 4 minutes depends on the intensity of the UV-radiation (performance of the UV-rays, the distance of the quartz tubes from the polymerized plastic coated mineral tooth) and must be varied according to the given conditions.

The most important feature when characterizing the invention is its industrial usefulness as well as the closed system of building up the mineral tooth (tension, shape of the dorsal and basal parts connected to the adhesive plastic parts) and the composition of the multiple component mixture (enabling the pressure-free polymerization and representing a favorable technological version) as well as the application of the pressure-free, crevice-free adhesive plastic part.

The advantage of this solution according to the invention is that by means of the multiple layer construction of the mineral tooth a reduction in tension is achieved from labially to dorsally and that the dorsal and basal layers respectively of the mineral tooth are adapted to the tensile behavior of the adhesive plastic part in a manner enabling that aimed at acting tensions between the silanized mineral tooth body and adhesive plastic part are causing a high adhesive strength.

Continuous movement of the mineral teeth in the silane solution and silanization for several times are the prerequisite for the achievement of a high affinity.

The composition of the multiple component mixture for the adhesive plastic part and its behavior with respect to viscosity requires that under suitable conditions of storage, this mixture has to be processed within 120 hours. The mineral tooth is shaped in an almost completely anatomical manner and the adhesive plastic part when applied to its dorsal and basal surfaces respectively forms with it a chemical compound. The mineral tooth with adhesive plastic part being industrially manufactured by the process according to the invention may be adapted to the base of a plastic prosthesis without additional expenditure in a dental laboratory and may be linked with it by chemical means like any known plastic tooth.

The mineral teeth according to the invention have neither any elements of anchoring by either precious- or base metals nor any diatonic or other forms of anchoring which would reduce the breaking strength of the mineral body.

We claim:

1. A process for producing an artificial tooth which comprises:

(a) providing a base mineral portion;

(b) fritting said base mineral portion at a temperature in the range of between 600° C. and 900° C., to produce a base mineral portion having grain sizes with a fractionation of from about 60 μm to about 100 μm;

(c) applying a silane layer to at least one surface of the base mineral portion, said silane layer being selected from the group consisting of ν-aminopropyltriethoxysilane, ν-glycidyloxypropyltrimethoxysilane, ν-methacryloxypropyltrimethoxysilane, and ν-aminopropyltrimethoxysilane;

(d) applying a plastic adhesive layer onto said silane layer, said plastic adhesive layer comprising 30% to 33% polymethacrylic acid methyl ester, 3% to 6% dioxane, 63% to 66% methacrylic acid methyl ester, 1% to 2% of a sensitizer, and 0.3% to 1% of a vapor pressure reducing substance; and (e) polymerizing said plastic adhesive layer with a quartz lamp radiating heat source using UV-rays for 3 to 6 minutes at a temperature of from 20° C. to 50° C., and under normal atmospheric pressure.

2. The process for producing an artificial tooth of claim 1, in which said base mineral portion is washed and degreased in an ultrasonic bath using a degreasing component selected from the group consisting of xylol and 1,1,2-trifluorotrichlorethane, prior to step (c).

3. The process for producing an artificial tooth of claim 2, in which the washing and degreasing takes place in the ultrasonic bath for about 10 minutes, after which the degreased base mineral portion is dried in an air stream for about 5 minutes.

4. The process for producing an artificial tooth of claim 1, in which the silane layer is applied according to step (c) by silanizing the base mineral portion in a silane solution comprising an about 1% water solution in an about 0.3% acetic acid solution, the silane solution being produced by mixing the silanes and the 0.3% acetic acid in a ratio of about 1:99.

5. The process for producing an artificial tooth of claim 4, in which the silane is ν-methacryloxypropyltrimethoxysilane.

6. The process for producing an artificial tooth of claim 4, in which the base mineral portion is inserted into the silane solution and joggled at least twice, each period of insertion and joggling being for about 5 minutes, with the base mineral portion being removed from the silane solution and dried at a temperature of about 110° C. for about 10 minutes, after each time period of insertion and joggling in the silane solution.

7. The process for producing an artificial tooth of claim 4, in which the silane solution is utilized for silanizing within 120 hours after preparation, to control the viscosity of the silanizing solution.

8. The process for producing an artificial tooth of claim 1, in which the plastic adhesive layer of step (d) is a multiple component mixture containing from 1% to 5% of a component selected from the group consisting of mineral filler material, previously silanized mineral fillers, silicate bonded color pigments, and mixtures thereof.

9. The process for producing an artificial tooth of claim 8, in which the previously silanized mineral fillers are selected from the group consisting of quartz and aluminum oxide, and mixtures thereof, with grain sizes of about 60 μm.

10. The process for producing an artificial tooth of claim 8, in which the silicate bonded color pigments have grain sizes of about 60 μm.

11. The process for producing an artificial tooth of claim 1, in which the plastic adhesive layer of step (d) comprises about 30.5% polymethacrylic acid methyl ester, about 63.9% methacrylic acid methyl ester, about 4.0% dioxane, about 1.3% UV sensitizer, and 0.3% of a vapor pressure reducing substance.

12. The process for producing an artificial tooth of claim 1, in which the plastic adhesive layer is polymerized according to step (e) for about 4 minutes.

13. The process for producing an artificial tooth of claim 1, in which the sensitizer is a compound of the formula

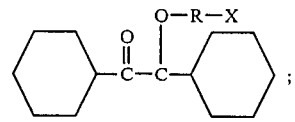

where R represents an alkylene group, an alkylene ether group, or polyalkylene ether groups, and X represents hydrogen, a hydroxy group, or a halogen.

14. An artificial tooth comprising a base mineral portion, said base mineral portion having grain sizes with a fractionation of from about 60 μm to about 100 μm and produced by fritting said base mineral portion at a temperature in the range of between 600° C. and 900° C., a silane layer on at least one surface of said base mineral portion, said silane layer being selected from the group consisting of γ-aminopropyltriethoxysilane, γ-glycidyloxypropyltrimethoxysilane, γ-methacryloxypropyltrimethoxysilane, and γ-aminopropyltrimethoxysilane, and a plastic adhesive layer on said silane layer, said plastic adhesive layer comprising 30% to 33% polymethacrylic acid methylester, 3% to 6% dioxane, 63% to 66% methacrylic acid methylester, 1% to 2% of a sensitizer, and 0.3% to 1% of a vapor pressure reducing substance, said plastic adhesive layer being a polymerized layer produced by polymerization with a quartz lamp radiating heat source using UV-rays for 3 to 6 minutes at a temperature of from 20° C. to 50° C., and under normal atmospheric pressure.

15. The artificial tooth of claim 14, in which the plastic adhesive layer is a multiple component mixture containing from 1% to 5% of a component selected from the group consisting of mineral filler material, previously silanized mineral fillers, silicate bonded color pigments, and mixtures thereof.

16. The artificial tooth of claim 15, in which the previously silanized mineral fillers are selected from the group consisting of quartz and aluminum oxide, and mixtures thereof, with grain sizes of about 60 μm.

17. The artificial tooth of claim 15, in which the silicate bonded color pigments have grain sizes of about 60 μm.

18. The artificial tooth of claim 14, in which the plastic adhesive layer comprises about 30.5% polymethacrylic acid methyl ester, about 63.9% methacrylic acid methylester, about 4.0% dioxane, about 1.3% UV sensitizer, and 0.3% of a vapor pressure reducing substance.

19. The artificial tooth of claim 14, in which the sensitizer is a compound of the formula

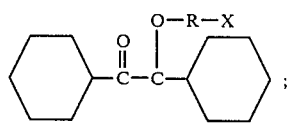

where R represents an alkylene group, an alkylene ether group, or polyalkylene ether groups, and X represents hydrogen, a hydroxy group, or a halogen.

* * * * *